(12) United States Patent
Kawamura (10) Patent No.: US 8,353,872 B2
(45) Date of Patent: Jan. 15, 2013

(54) INFUSION PUMP

(75) Inventor: Yasuhiro Kawamura, Tokyo (JP)

(73) Assignee: SIMS, Tokyo (JP)

(*) Notice: Subject to any disclaimer, the term of this patent is extended or adjusted under 35 U.S.C. 154(b) by 0 days.

(21) Appl. No.: 13/292,710

(22) Filed: Nov. 9, 2011

(65) Prior Publication Data

US 2012/0053560 A1 Mar. 1, 2012

Related U.S. Application Data (63) Continuation of application No. 12/972,348, filed on Dec. 17, 2010.

(60) Provisional application No. 61/287,881, filed on Dec. 18, 2009, provisional application No. 61/287,903, filed on Dec. 18, 2009, provisional application No. 61/287,912, filed on Dec. 18, 2009, provisional application No. 61/287,991, filed on Dec. 18, 2009.

(51) Int. Cl.
*A61M 1/00* (2006.01)

(52) U.S. Cl. ........................ 604/151; 604/131

(58) Field of Classification Search .......... 604/131, 604/151; 417/413.1, 413.2
See application file for complete search history.

(56) References Cited

U.S. PATENT DOCUMENTS

| | | | |
|---|---|---|---|
| 3,963,380 A | 6/1976 | Thomas, Jr. et al. | |
| 3,980,082 A | 9/1976 | Miller | |
| 4,080,966 A | 3/1978 | McNally et al. | |
| 4,468,219 A | 8/1984 | George et al. | |
| 4,596,575 A | 6/1986 | Rosenberg et al. | |
| 4,756,706 A | 7/1988 | Kerns et al. | |
| 4,898,578 A | 2/1990 | Rubalcaba, Jr. | |
| 4,938,742 A | 7/1990 | Smits | |
| 4,944,659 A | 7/1990 | Labbe et al. | |
| 5,171,132 A * | 12/1992 | Miyazaki et al. | 417/413.1 |
| 5,205,819 A | 4/1993 | Ross et al. | |
| 5,256,157 A | 10/1993 | Samiotes et al. | |
| 5,713,856 A | 2/1998 | Eggers et al. | |
| 5,840,062 A | 11/1998 | Gumaste et al. | |
| 5,984,894 A | 11/1999 | Poulsen et al. | |
| 6,085,574 A | 7/2000 | Neftel | |
| 6,102,678 A | 8/2000 | Peclat | |
| 6,813,944 B2 | 11/2004 | Mayer et al. | |
| 7,592,740 B2 | 9/2009 | Roe | |
| 7,601,148 B2 | 10/2009 | Keller | |
| 2003/0004492 A1 | 1/2003 | Munis et al. | |
| 2003/0045858 A1 | 3/2003 | Struys et al. | |

(Continued)

FOREIGN PATENT DOCUMENTS

GB 2 260 622 A 4/1993

(Continued)

OTHER PUBLICATIONS

Gonzalez et al, "Simulation of MEMS Piezoelectric Micropump for Biomedical Applications", http://www.algor.com/news_pub/tech_white_papers/MEMS_micropump/default.asp, Jun. 10, 2008.*

(Continued)

*Primary Examiner* — Bhisma Mehta
(74) *Attorney, Agent, or Firm* — Inskeep IP Group, Inc.

(57) ABSTRACT

Infusion pumps according to the present invention maximize fluid throughput while minimizing vaporization of gas by employing specific flow path architecture, flow path dimensional ranges, and voltage and frequency ranges for activation of piezoelectric bodies.

15 Claims, 7 Drawing Sheets

U.S. PATENT DOCUMENTS

| | | |
|---|---|---|
| 2003/0130624 A1 | 7/2003 | Kowalik et al. |
| 2003/0130625 A1 | 7/2003 | Jacobson et al. |
| 2003/0140928 A1 | 7/2003 | Bui et al. |
| 2003/0141981 A1 | 7/2003 | Bui et al. |
| 2004/0000843 A1 | 1/2004 | East |
| 2004/0121767 A1 | 6/2004 | Simpson et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2005/0065817 A1 | 3/2005 | Mihai et al. |
| 2005/0101907 A1 | 5/2005 | Sondeen et al. |
| 2005/0247558 A1 | 11/2005 | Anex et al. |
| 2006/0064053 A1 | 3/2006 | Bollish et al. |
| 2006/0100580 A1 | 5/2006 | Muller |
| 2006/0235353 A1 | 10/2006 | Gelfand et al. |
| 2006/0264829 A1 | 11/2006 | Donaldson |
| 2007/0065308 A1* | 3/2007 | Yamamoto et al. ........ 417/413.1 |
| 2007/0128055 A1* | 6/2007 | Lee ............................ 417/413.1 |
| 2007/0255199 A1 | 11/2007 | Dewey |
| 2007/0270748 A1 | 11/2007 | Dacquay et al. |
| 2008/0097291 A1 | 4/2008 | Hanson et al. |
| 2008/0097375 A1 | 4/2008 | Bikovsky |
| 2008/0220092 A1 | 9/2008 | DiPierro et al. |
| 2008/0255502 A1 | 10/2008 | Jacobson et al. |
| 2009/0105650 A1 | 4/2009 | Wiegel et al. |
| 2009/0124994 A1 | 5/2009 | Roe |
| 2009/0164163 A1 | 6/2009 | Wang et al. |
| 2009/0177188 A1 | 7/2009 | Steinkogler |
| 2009/0241952 A1 | 10/2009 | Nicolazzi |
| 2009/0254025 A1 | 10/2009 | Simmons |

FOREIGN PATENT DOCUMENTS

| | | |
|---|---|---|
| JP | 2006-136376 A | 6/2006 |
| JP | 2010-063767 A | 3/2010 |
| WO | WO2004/070994 A2 | 8/2004 |
| WO | WO2010/029931 A1 | 3/2010 |

OTHER PUBLICATIONS

United States Patent and Trademark Office, U.S. Appl. No. 60/528,106, filed Dec. 8, 2003, 119 pages.

United States Patent and Trademark Office, U.S. Appl. No. 60/488,273, filed Jul. 18, 2003, 77 pages.

United States Patent and Trademark Office, U.S. Appl. No. 60/444,350, filed Feb. 1, 2003, 70 pages.

United States Patent and Trademark Office, U.S. Appl. No. 60/377,027, filed Apr. 30, 2002, 17 pages.

United States Patent and Trademark Office, U.S. Appl. No. 60/376,655, filed Apr. 30, 2002, 50 pages.

United States Patent and Trademark Office, U.S. Appl. No. 60/376,625, filed Apr. 30, 2002, 64 pages.

WIPO, U.S. International Search Authority, International Search Report and Written Opinion mailed May 20, 2011 in International Patent Application No. PCT/US2010/061162, 8 pages.

WIPO, U.S. International Search Authority, International Search Report and Written Opinion mailed Feb. 28, 2011 in International Patent Application No. PCT/US2010/061167, 9 pages.

WIPO, U.S. International Search Authority, International Search Report and Written Opinion mailed Feb. 17, 2011 in International Patent Application No. PCT/US2010/061158, 9 pages.

* cited by examiner

INFUSION PUMP

RELATED APPLICATIONS

This application is a continuation of U.S. patent application Ser. No. 12/972,348 filed Dec. 17, 2010 entitled Infusion Pump, which claims priority to U.S. Provisional Application Ser. No. 61/287,881 filed Dec. 18, 2009, entitled MEMS Pump for Medical Infusion Pump; U.S. Provisional Application Ser. No. 61/287,903 filed Dec. 18, 2009, entitled Pump Stay, U.S. Provisional Application Ser. No. 61/287,912 filed Dec. 18, 2009, entitled Micro Infusion Pump System Software; U.S. Provisional Application Ser. No. 61/287,991 filed Dec. 18, 2009, entitled Central Venous Pressure Monitoring Using Micro Infusion Pump, the contents of which are each incorporated in their entirety herein.

FIELD OF THE INVENTION

The present invention relates to medical infusion pumps and related methods and, more particularly, to infusion pumps employing the piezoelectric effect for medical and healthcare related applications.

BACKGROUND OF THE INVENTION

Fluid pumps can be driven based on various design principles including the piezoelectric effect. The piezoelectric effect can be employed to indirectly cause fluid flow, for example a piezoelectric driven motor or actuator can be used to linearly displace a plunger to push fluid from a reservoir or to rotate a rotor in a peristaltic-type pump. For example, U.S. Publication Nos. 2009/0124994 to Roe and 2009/0105650 to Wiegel et al., and U.S. Pat. Nos. 7,592,740 to Roe, and 6,102,678 to Perclat teach the application of such technologies to infusion pumps used in the medical and health care industries.

Alternatively, the piezoelectric effect can be employed to cause fluid flow through the direct manipulation of a fluid chamber or flow path, for example through vibration of an internal surface of a fluid chamber. Such microelectromechanical system, or MEMS, micropumps can be fabricated using known integrated circuit fabrication methods and technologies. For example, using integrated circuit manufacturing fabrication techniques, small channels can be formed on the surface of silicon wafers. By attaching a thin piece of material, such as glass, on the surface of the processed silicon wafer, flow paths and fluid chambers can be formed from the channels and chambers. A layer of piezoelectric material, or a piezoelectric body such as quartz, is then attached to the glass on the side opposite the silicon wafer. When a voltage is applied to the piezoelectric body, a reverse piezoelectric effect, or vibration, is generated by the piezoelectric body and transmitted through the glass to the fluid in the chambers. In turn, a resonance is produced in the fluid in the chambers of the silicon wafer. Through the inclusions of valves and other design features in the fluid flow paths, a net directional flow of fluid through the chambers formed by the silicon wafer and the glass covering can be achieved.

MEMS micropumps have become an established technology in the inkjet printer industry. Technological developments relating to increased definition and ink throughput for piezoelectric micropumps, or MEMS micropumps, for inkjet printers have achieved more precise printing with smaller ink throughputs. For example, it has become possible to control the ink throughput of inkjet printers employing MEMS micropumps at the picoliter level. Furthermore, in order to address the problems associated with uneven printing in inkjet printers due to the vaporization of gas dissolved in the ink, considerable development has also been directed to providing inkjet printers with structures for degassing the ink.

MEMS micropumps employing the piezoelectric effect have also been contemplated for use in small and large-volume infusion pumps, i.e. pump systems that are typically employed to infuse fluids, medications, and nutrients into a patient's circulatory system. For example, with respect to small-volume infusion systems, U.S. Pat. Nos. 3,963,380 to Thomas, Jr. et al.; 4,596,575 to Rosenberg; 4,938,742 to Smits; 4,944,659 to Labbe et al.; 5,984,894 to Poulsen et al.; and 7,601,148 to Keller all describe various micropumps intended for implantation into a patient in order to administer small amounts of pharmaceuticals, such as insulin. Similarly, U.S. Publication No. 2007/0270748 to Dacquay et al. describes a piezoelectric micropump integrated into the tip of a syringe for very low volume delivery of ophthalmic pharmaceuticals to a patient's eye.

In contrast to inkjet printers and small-volume infusion micropumps, large-volume infusion pumps must be operable to provide significantly increased fluid throughput. However, as fluid throughput, or fluid flow rates are increased, the potential for the vaporization of dissolved gas correspondingly increases. Those skilled in the art will recognize that the vaporization of dissolved gas within the fluid flow paths of infusion pump systems presents a significant health hazard to patients receiving infusions. While the problems associated with the vaporizations of dissolved gas in inkjet printer micropumps, systems in which fluid throughputs are relatively low, has largely been addressed through the development of degassing technologies, satisfactory solutions have not been presented for high-throughput micropumps, such as infusion pumps, used in the health and medical industry. U.S. Publication No. 2006/0264829 to Donaldson and U.S. Pat. No. 5,205,819 to Ross et al. described large-volume infusion systems employing piezoelectric micropumps; however, neither of these systems provides solutions directed to overcoming the problems associated with vaporization of dissolved gas at high fluid throughputs.

What is needed in the field is a highly accurate infusion pump system that provides high fluid throughput while reducing or eliminating the risk of the vaporization of dissolved gasses within the fluid flow path.

OBJECTS AND SUMMARY OF THE INVENTION

The infusion pumps according to the present invention provide highly accurate infusion pump systems that provides high fluid throughput while reducing or eliminating the risk of vaporization of dissolved gasses within the fluid flow path. Infusion pumps according to the present invention achieve these advances by employing specific flow path architecture, flow path dimensional ranges, and voltage and frequencies ranges that, relative to one another, serve to provide an infusion pump that maximize fluid throughput while minimizing vaporization of gas.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Infusion pumps according to the present invention provides unique flow path and fluid chamber structure in order to provide highly accurate fluid flow and relatively high fluid throughput while reducing or eliminating the risk of vaporization of dissolved gas within the fluid flow path.

Figure 1:
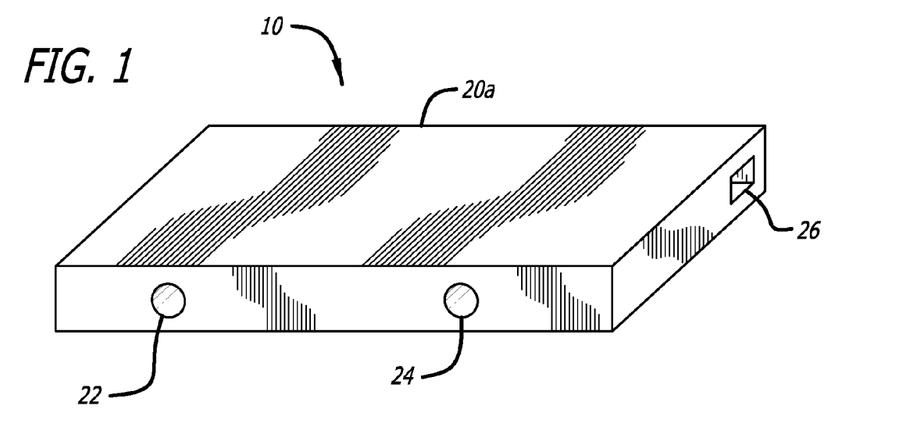
FIG. 1 is a perspective view of an infusion pump according to one embodiment of the present invention.
Figure 2A:
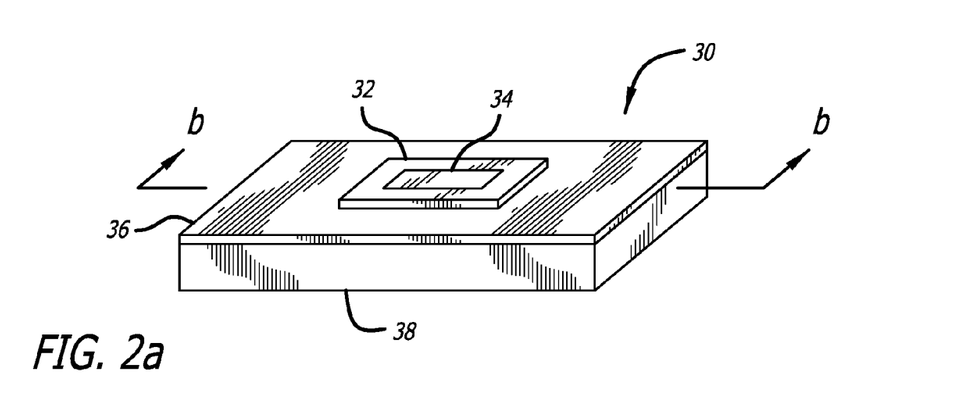
FIG. 2a is a perspective view of a micropump according to one embodiment of the present invention.
Figure 2B:
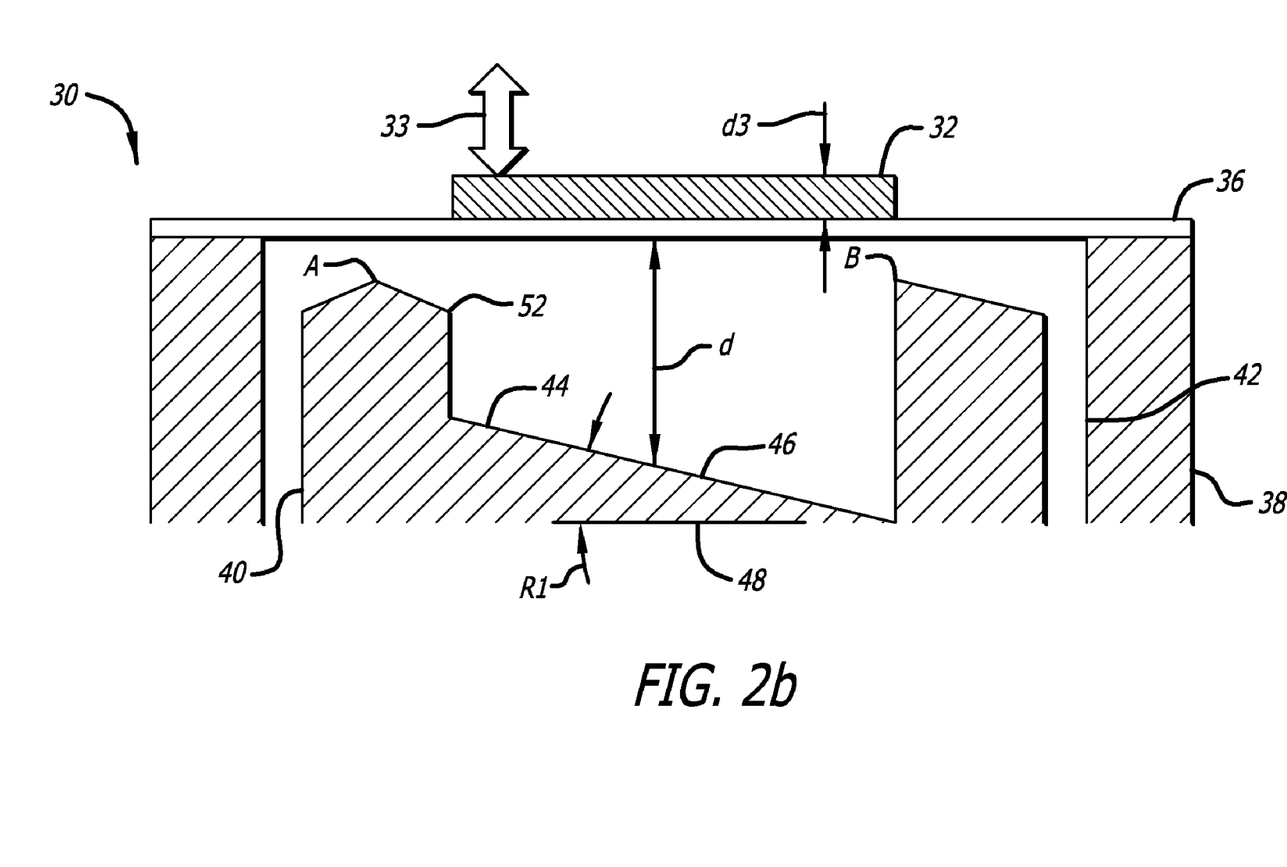
FIG. 2b is a cross-sectional view taken along line b of FIG. 2a of a micropump according to one embodiment of the present invention.

As shown in FIG. 1, an infusion pump 10 according to one embodiment of the present invention comprises a pump body 20a having an inlet port 22, an outlet port 24, and a communication port 26. Situated within body 20a is a MEMS micropump. As shown in FIG. 2a and the cross-sectional view of FIG. 2b taken along line b of FIG. 2a, the MEMS micropump, or micropump, 30 comprises a piezoelectric body 32 having a thickness indicated as d3 attached to one side of a vibration layer 36. The vibration layer 36 may be fabricated from glass, quarts, alloy or a polymer-based material. An opposite side of the piezoelectric body 32 is in electrical contact with an electrode 34, and an opposite side of the vibration layer 36 is affixed to a pump base 38. As shown in FIG. 2b and the plan views of the pump base 38 shown in FIGS. 2c and 2d, formed within the pump base 38 are flow channels and fluid chambers. More particularly, the pump base 38 comprises inlet channel 40, outlet channel 42, and chamber 44. The chamber 44 has a length l1 and a width l2. A distance from a bottom 46 of the chamber 44 to a top of the chamber 44 formed by the vibration layer 36 is indicated as a depth d. It will be understood that the depth d is determined in the approximate center or middle of the chamber 44. An inclination or angle of the bottom 46 of the chamber 44 relative to the bottom 48 of the pump base 38 is indicated as an angle R1. As shown in FIG. 2b, in one embodiment, the angle of the bottom 46 of the chamber 44 relative to the bottom 48 of the pump base results in the chamber 44 being shallowest proximate the inlet channel 40 and deepest proximate the outlet channel 42. While only one angle R1 has been described, it will be understood that the bottom 46 of the chamber 44 may be angled relative to the bottom 48 of the pump base 38 in more than one plane of reference. The inlet channel 40 and outlet channel 42 are each formed on opposite sidewalls of the chamber 44, are each continuously open to fluid flow, and each comprise a differently configured channel constriction.

The piezoelectric body 32 may comprise various known materials having piezoelectric properties, including naturally occurring crystals such as quartz, man-made crystals and man-made ceramics and polymers.

The pump base 38 may be fabricated from silicon; such as the silicon wafers employed in known integrated circuit fabrication techniques, or may be fabricated from other sufficiently rigid materials such as various metals, alloys, and polymers. It will be understood that, based upon the specific material(s) from which the pump base 38 is fabricated as well as, the specific technique employed for creating the channels and chambers within the pump base 38, the surfaces of the channels and chambers may be smooth and/or stepped. For example, if the pump base 38 is fabricated using known integrated circuit fabrication techniques, the inclination or angle of the bottom 46 of the chamber 44 may be formed by removing silicon in defined steps according to the various masks employed. Accordingly, the sloped surface of the bottom 46 of the chamber 44 would be stepped rather than smooth. Conversely, if the pump base 38 is fabricated from a metal or alloy, the inclination or angle of the bottom 46 of the chamber 44 may be formed such that the surface of the bottom 46 of the chamber 44 is smooth.

Formed within the inlet channel 40 is a constriction A, and formed within the outlet channel 42 is a constriction B. It will be noted that the constrictions A and B may narrow in a horizontal, vertical, or horizontal and vertical directions. A length of the inlet channel 40 from the constriction A to the side 50 of the chamber is indicated as l3. A width of the inlet channel 40 upstream of the constriction A is indicated as L1, and a width of the constriction A is indicated as L2.

Figure 2C:
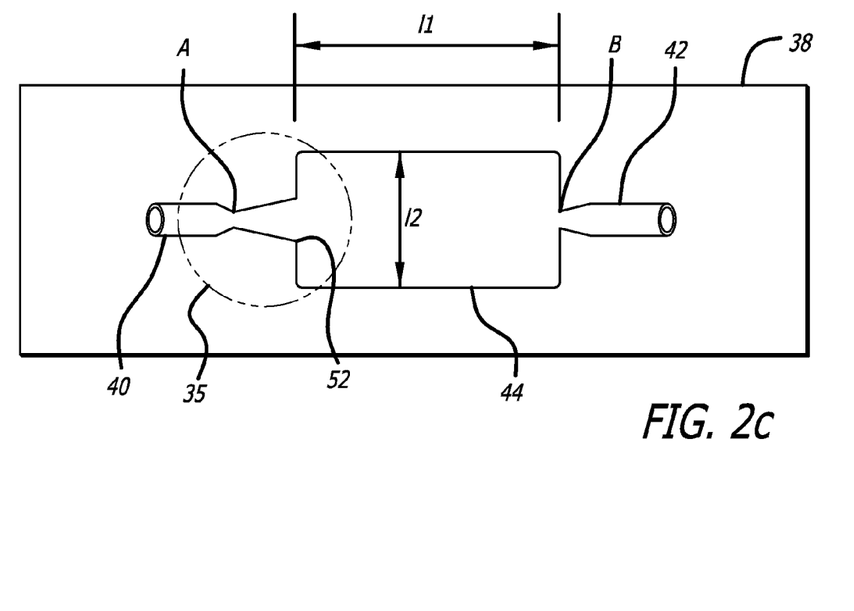
FIG. 2c is a plan view of a pump base of a micropump according to one embodiment of the present invention.
Figure 2D:
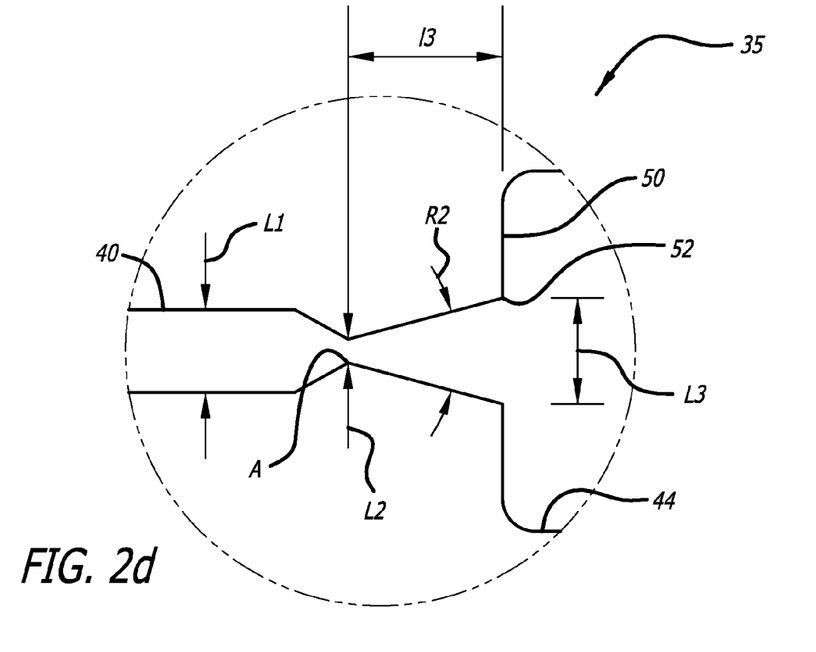
FIG. 2d is an expanded plan view of a portion 35 of FIG. 2c of a pump base of a micropump according to one embodiment of the present invention.

As shown best in FIG. 2d, between the constriction A and a chamber inlet 52, the inlet channel 40 has a funnel-like or triangular form. An angle defined by this funnel-like form of inlet channel 40 between the constriction A and a chamber inlet 52 is indicated as R2. The width of the chamber inlet 52 is indicated as L3. In operation, the piezoelectric body 32 vibrates in the directions indicated by arrow 33 as a result of a voltage V applied to the piezoelectric body 32 through the electrode 34 at a frequency n. The vibration of the piezoelectric body 32 is transferred to a fluid within the chamber 44 through the vibration layer 36 thereby producing a resonance in the fluid within the chamber 44. A pumping, or a net directional flow, of the fluid within the chamber 44 occurs in accordance with the resistances created by the constrictions A and B formed in the inlet channel 40 and the outlet channel 42 respectively.

It will be understood that the resonance created within the chamber 44, and thereby the flow of fluid through the micropump 30, is influenced by geometry of the chamber 44 and inlet and outlet channels 40 and 42. Also influencing the resonance is the frequency, the voltage, and the shape of the wave that contribute to the piezoelectric effect of the piezoelectric body. Therefore, micropumps 30 according to the present invention are optimized with respect to the following parameters: (1) the length l1 of the chamber 44; (2) the width l2 of the chamber 44; (3) the depth d of the chamber 44; (4) the angle R1 defined by the bottom 46 of the chamber 44 relative to the bottom 48 of the pump base 38; (5) the number of micropumps or micropump chambers 44 employed in the system; (6) the configuration of the constriction A relevant to the inlet channel 40 up stream of the constriction A; (7) the configuration of the constriction A relevant to the chamber inlet 52 downstream of the constriction A; vibration layer 36 (8) the thickness d3 of the piezoelectric body 32 and the number of piezoelectric bodies 32 employed; and (9) the voltage V applied to the piezoelectric body 32 at the frequency n.

Turning first to the relevant parameters regarding the chamber 44 of the micropump 30, in order to achieve a high fluid throughput, micropumps 30 according to the present invention employ a relatively large-volume chamber 44. The shape of the chamber 44, that is to say, the relationship of the length to width to depth of the chamber 44 is an important consideration in order to optimize the resonance phenomena generated in the fluid within the chamber 44. For example, the depth d of the chamber 44 influences the magnitude of the resonance which, in turn, increases fluid throughput. However, at extreme magnitudes, the resonance of the liquid in the chamber 44 will undesirably occur only at the upper layer of the fluid and fluid throughput will decrease.

Relative to the other optimized parameters herein provided for micropumps 30 according to the present invention, the distance d from a bottom 46 of the chamber 44 to a top of the chamber 44 formed by the vibration layer 36 is preferably 50 to 300 micrometers and more preferably 100 to 200 micrometers. The length l1 of the chamber 44 is preferably within the range of 1 to 30 millimeters, and the width l2 of the chamber 44 is preferably within the range of 1 to 5 millimeters. Within the preferred range on depths d, a preferred range of length to width ratios is 1:1 to 6:1 and more preferably 4:1. For example, an optimized chamber 44 may have a length l1 of 4 millimeters and a width l2 of 1 millimeters and a depth of 200 micrometers.

Also related to the shape of the chamber 44 is the angle R1 defined by the bottom 46 of the chamber 44 relative to the bottom 48 of the pump base 38. The angle R1 results in the chamber 44 being shallowest proximate the inlet channel 40 and deepest proximate the outlet channel 42. Hence, the angle R1 serves to bias the resonance towards the outlet channel 42 side of the chamber 44, i.e. towards the right side of the chamber 44 as shown in FIGS. 2b and 2c. While a greater angle R1 increases the fluid throughput, at overly steep angles, the resonance at the downstream side of the chamber 44 and thereby fluid throughput will tend to decrease. Relative to the other optimized parameters herein provided for micropumps 30 according to the present invention, the angle R1 defined by the bottom 46 of the chamber 44 relative to the bottom 48 of the pump base 38 is preferably in the range of zero to 50 degrees and more preferably between 0.01 to 10 degrees.

Figure 3:
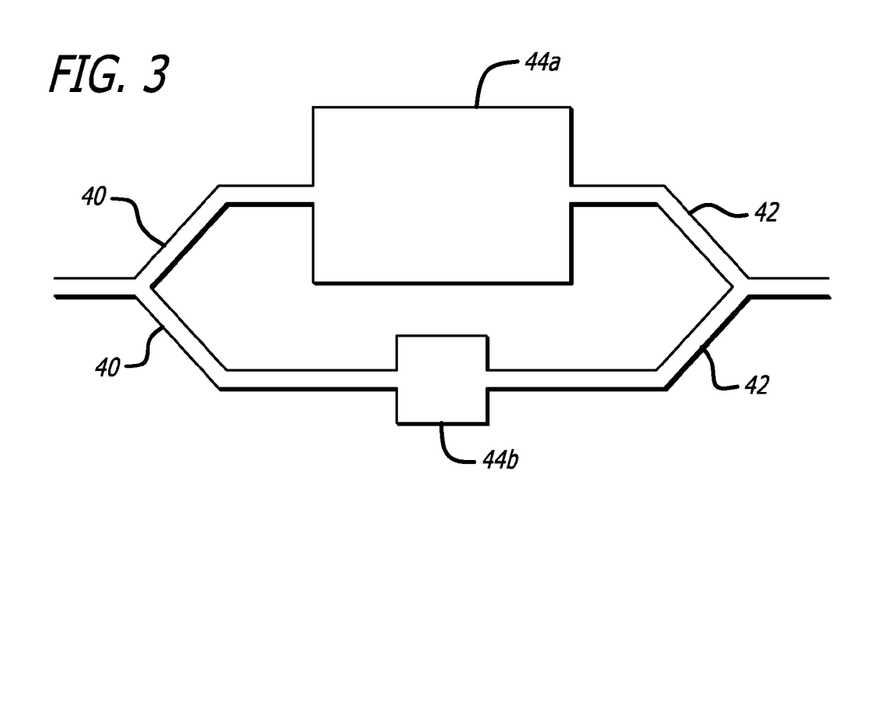
FIG. 3 is a plan view of flow channels and cambers of a micropump according to one embodiment of the present invention.

In situations in which one micropump 30 does not provide the desired throughput, a micropump 30 having increased throughput can be formed by combining a number N of chambers 44 in parallel or in series. In such multi-chamber 44 pumps, identical chambers 44 may be combined, or as shown in FIG. 3, chambers 44 having differing sizes and throughputs may be combined. Pumps having a plurality of chambers 44 of different sizes or dimensions operable of providing different fluid throughputs, allow for a more precise throughput control and a broader throughput range. For example, in cases such as those wherein the throughput is to be varied, advantages such as better precision and a wider range of throughputs can be achieved by combining a 100 milliliter per hour chamber 44a and a 10 milliliter per hour chamber 44b. In medical settings, this is advantageous in so much as it is not necessary to change pumps, even when changing from 100 milliliter per hour of a drug to 10 milliliter per hour of a drug.

Turning now to the relevant parameters regarding the constriction A and the inlet channel 40 upstream of the constriction A. It is noted that a smaller width L2 of the constriction A is associated with increased throughput, however, a smaller width L2 is also associated with increased negative pressure downstream from the constriction A. This, in turn, results in an increased undesirable vaporization of dissolved gas. Relative to the other optimized parameters herein provided for pumps according to the present invention, the width L2 of the constriction A is preferably in 30 to 200 micrometers and more preferably 40 to 80 micrometers, for example 50 micrometers. The width L1 of the inlet channel 40 upstream of the constriction A is preferably 50 to 300 micrometers and more preferably 80 to 100 micrometers, for example 80 micrometers. The range of the ratio L2:L1 is preferably 0.13 to 0.67.

Turning now to the relevant parameters regarding the constriction A and the inlet channel 40 downstream of the constriction A. The constriction width angle R2 is defined by this funnel-like, or triangular, form of inlet channel 40 between the constriction A and the chamber inlet 52. Alternatively stated, the constriction width angle R2 refers to the angle formed at the apex of a triangle formed by the length l3 and the width L3. While increasing the constriction width angle R2 achieves a greater fluid throughput, increasing the constriction width angle R2 also increases the negative pressure upstream of the constriction A. The angle R2 is determined by the formula:

$$R2 = 2(\text{tangent})\left(\frac{(L3 - L2)0.5}{l3}\right)$$

Alternatively stated the angle R2 is equal to two times the tangent of L3 minus L2 times 0.5 divided by l3. Relative to the other optimized parameters herein provided for pumps according to the present invention, width L2 of the constriction A is preferably in 30 to 200 micrometers and more preferably 50 micrometers; width L3 of the chamber inlet 52 is preferably 50 to 300 micrometers and more preferably 80 micrometers; and the length l3 of the inlet channel 40 from the constriction A to the chamber outlet 52 is preferably 1 to 15 millimeters and more preferably 10 millimeters. The constriction width angle R2 is preferably 0.00001 to 10 degrees and more preferably 0.0005 degrees.

Turning now to the relevant parameters of the piezoelectric body 32, employing a thicker piezoelectric body 32 results in increased vibration which causes greater resonance to be produced thereby increasing fluid throughput. However, increased resonance may also result in increased negative pressure at the constriction A, thereby causing vaporization of dissolved gas. In order to increase the pumping rate, two or three piezoelectric bodies having thicknesses of 0.1 millimeter to 1 millimeter can be stacked.

Finally, with respect to the voltage V applied to the piezoelectric body 32 at the frequency n, increases in frequency and/or voltage with initially increase fluid throughput. Relative to the other optimized parameters herein provided for micropumps 30 according to the present invention, the frequency n is preferably in the range of 50 to 4500 hertz. With respect to voltage, the higher the voltage, the greater the amplitude at which the piezoelectric body will vibrate, which will cause an increase the resonance phenomena produced within the chamber, and increase fluid flow. However, strong resonance phenomena will also produce a greater negative pressure at the constriction A, which will result in vaporization of dissolved gasses. Accordingly, relative to the other optimized parameters herein provided for pumps according to the present invention, the voltage V is preferably in the range of 20 to 100 volts.

Figure 4:
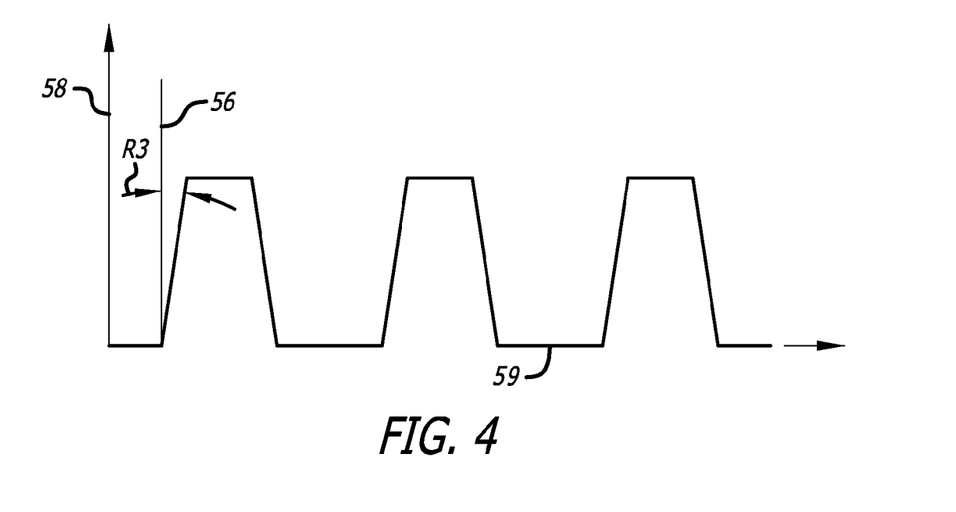
FIG. 4 is a graphical representation of a power provided to a micropump according to one embodiment of the present invention.

Furthermore, the manner in which the voltage is applied also influences the throughput of micropumps according to the present invention. For example, the negative pressure in the area of the constriction A and thus the vaporization of dissolved gas is controlled by controlling the rate of rise of the voltage V. FIG. 4 shows the manner in which the voltage is preferably applied. In the graph provided in FIG. 4, the horizontal axis 59 represents the passage of time and the vertical axis 58 represents increasing voltage. Line 56 is provided as a reference line from which angle R3 is determined. Relative to the other optimized parameters herein provided for pumps according to the present invention, in order to reduce or prevent vaporization of dissolved gas, angle R3 is preferably in the range of 3 to 45 degrees.

The infusion pumps 10 according to the present invention are operable to provide fluid flow rates of up to approximately 280 milliliters per hour and greater. It will be understood, however, that the flow rate achieved by the infusion pump 10 is dependent upon the back pressure imparted by the patient's circulatory system. Accordingly, as the back pressure imparted on the infusion pump 10 increases, the control factors provided to the micropump 30 must be changed in order achieve the desired flow rate while overcoming such back pressure. For example, while maintaining all other design parameters and control factors constant, at back pressure of zero kilopascal, the infusion pump 10 according to the present invention may achieve a flow rate of approximately 780 microliters per minute at a frequency of 50 hertz, or Hz; 1,610 microliters per minute at a frequency of 100 Hz; and 1,930 microliters per minute at a frequency of 150 Hz. At back pressure of 60 kilopascal, the infusion pump 10 according to the present invention may achieve a flow rate of approximately 230 microliters per minute at a frequency of 50 Hz; 440 microliters per minute at a frequency of 100 Hz; and 630 microliters per minute at a frequency of 150 Hz.

Figure 5A:
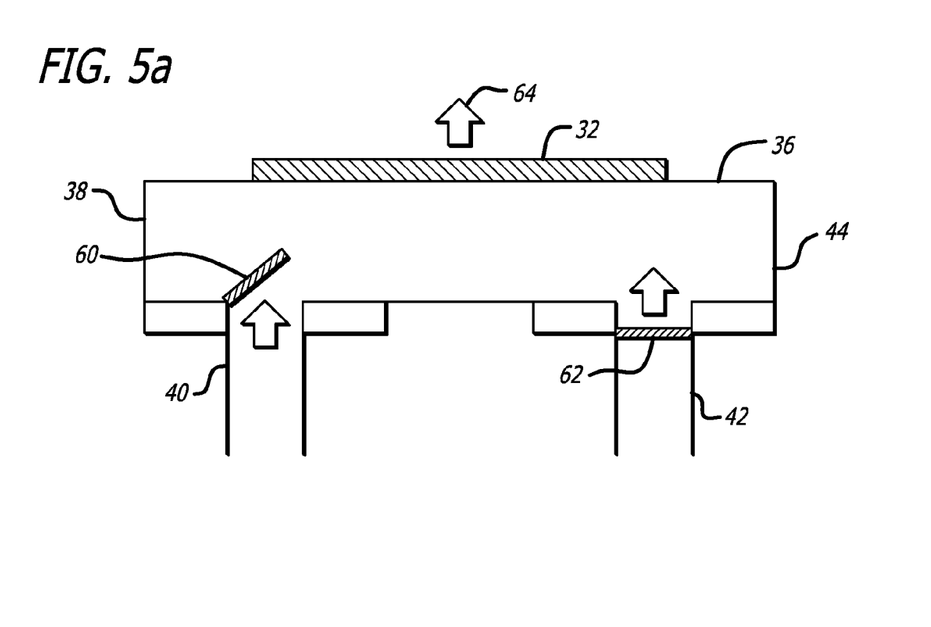
FIGS. 5a and 5b are cross-sectional views of a micropump according to one embodiment of the present invention.
Figure 5B:
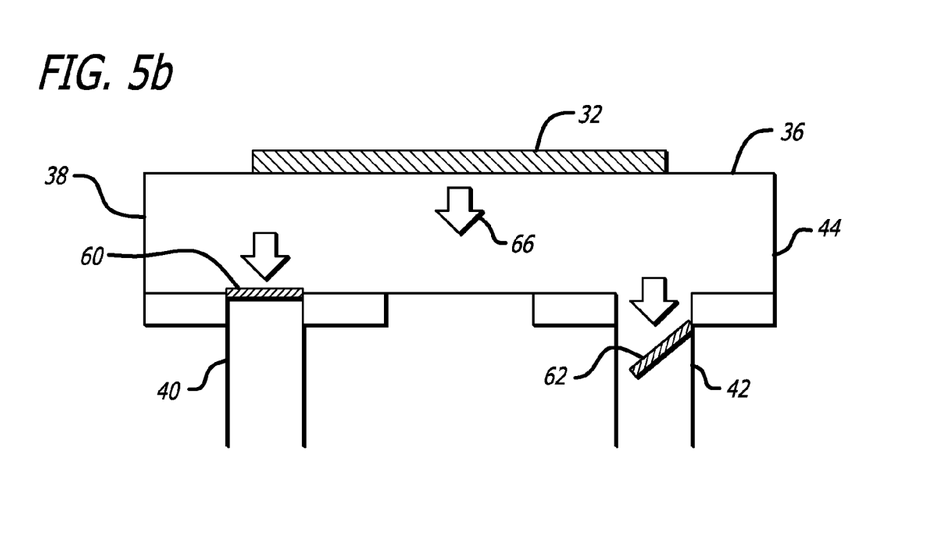

In yet another embodiment of the present invention, as shown in FIGS. 5a and 5b, a micropump 330 comprises the piezoelectric body 32 attached to one side of the vibration layer 36. An opposite side of the vibration layer 36 is affixed to the pump base 38. The pump base 38 comprises the inlet channel 40, the outlet channel 42, and the chamber 44. In contrast to the micropump 30 described above, the micropump 330 further comprises inlet valve 60 and outlet valve 62. The inlet valve 60 and the outlet valve 62 are operable to transpose as shown in FIGS. 5a and 5b.

In operation, when the piezoelectric body 32 is manipulated in the direction of arrow 64, chamber 44 becomes negatively pressurized and inlet valve 60 opens allowing fluid flow into the chamber 44. Conversely, outlet valve 62 is pulled closed thereby discouraging any backflow of fluid in to the chamber 44. When the piezoelectric body 32 is manipulated in the direction of arrow 66, chamber 44 becomes positively pressurized. Inlet valve 60 is pushed closed thereby preventing flow out through the inlet channel 40. Conversely, outlet valve 62 is opened to allow fluid flow through the outlet channel 42.

It will be understood that features, such as the valves 60 and 62, described above with respect to micropump 330 may be combined with any of the design features described with respect to micropumps 30 and vice versa in order to achieve micropumps according to the present invention.

Figure 6:
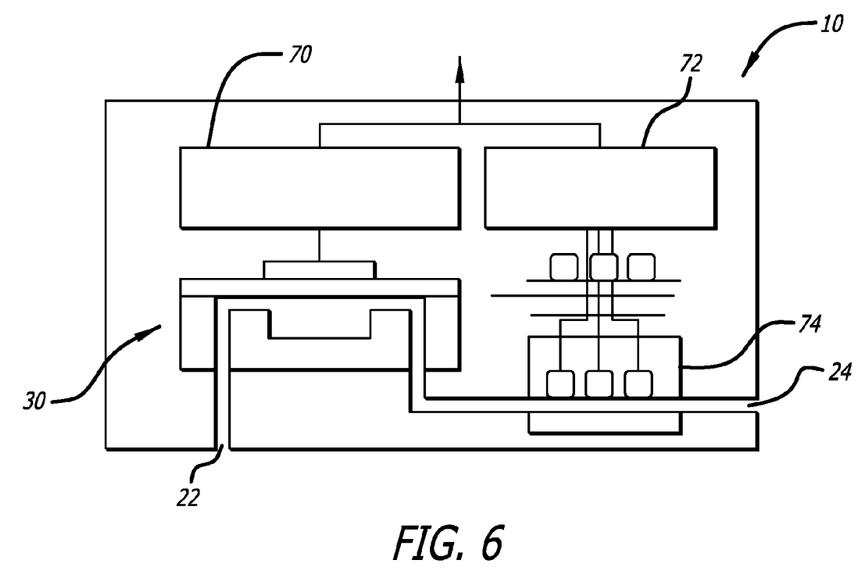
FIG. 6 is a plan view of a micropump according to one embodiment of the present invention.

As shown in FIG. 6, the infusion pump 10 according to the present invention further comprises a first circuit 70, a second circuit 72 and flow meter 74. The first circuit provides power to the electrode 34, shown in FIG. 2a, and the second circuit 72 provides power to the flow meter 74 and AC/DC conversion of the data from the sensors associated with the flow meter 74. The first and second circuits 72 and 74 are accordingly in electrical communication with a power source such as a wall mounted plug, a battery, or a combination thereof. The obvious advantage of an infusion pump 10 employing a battery is the corresponding mobility of the infusion pump 10 while maintaining uninterrupted flow of infusion fluids.

The flow meter 74 associated with the infusion pump 10 may comprise a variety of know flow meters. The flow meter 74 may comprise a variety of known flow meters. For example, the flow meter 74 may be configured to determine fluid flow rates by employing a heater that heats the fluid being monitored and senses the flow of the heated fluid downstream of the heater. Such flow meters are available from Sensirion AG of Switzerland and Siargo Incorporated of the United States of America and are described in greater detail in at least U.S. Pat. No. 6,813,944 to Mayer et al. and U.S. Publication No. 2009/0164163, which are herein incorporated by reference. Alternatively, the flow meter 74 may be configured to employ two pressure sensors positioned on each side of a constriction within the fluid flow path. Fluid flow rates are determined by the relative difference between the pressure sensors and changes thereof.

Figure 7:
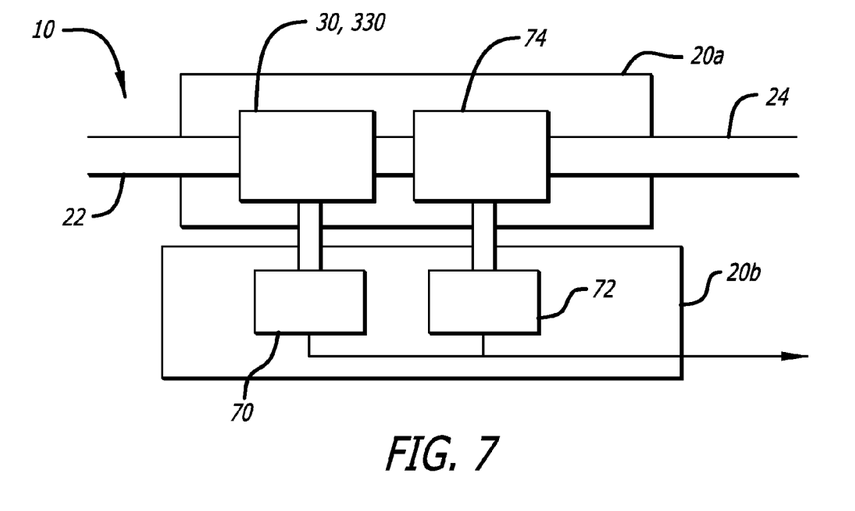
FIG. 7 is a plan view of a micropump according to one embodiment of the present invention.

It is noted that while infusion pump 10 has been depicted as a single unit or component in FIGS. 1 and 6, certain elements of the infusion pump 10 may be compartmentalized within different components or bodies. For example, FIG. 7 shows an infusion pump 10 in which first and second circuits 70 and 72, respectively, housed in body 20b separate from the micropump 30, 330 and the flow meter 74 which are contained in body 20a. Such as system is advantageous for several reasons. For example, it may be preferable to fabricate body 20a comprising the micropump 30, 330 and the flow meter to be disposable. Accordingly, risk of contamination and the costs associated with cleaning and preparing the micropump 30, 330 and flow meter 74 for use with different patients can be decreased. However, in order that the cost of production of the infusion pump may be minimized, it may be desirable to make as few as possible of the components of the infusion pump 10 disposable. Accordingly, body 20b in which the circuits 70 and 72 are contained may be considered nondisposable, or reusable.

The infusion pump 10 of the present invention comprising multiple bodies, such as bodies 20a and 20b, may employ structures to establish electrical communication between one another. For example, as shown in FIG. 1, body 20a may comprise a communication port 26 through which the first and second circuits 70 and 72 may be placed in electrical communication with the electrode 34 of the micropump 30 and the flow meter 74, respectively. The communication port 26 may be fabricated from a variety of electrical connectors/terminals and wire types known in the art.

Figure 8A:
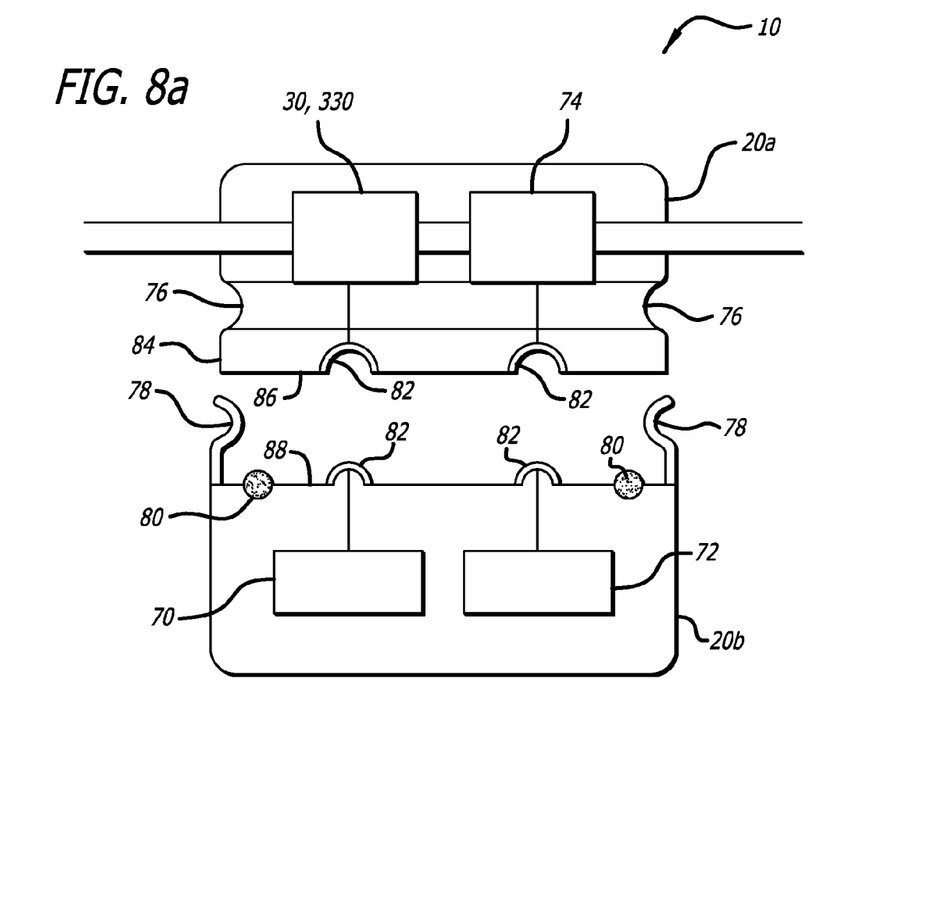
FIG. 8a is a side elevation view of a micropump according to one embodiment of the present invention.
Figure 8B:
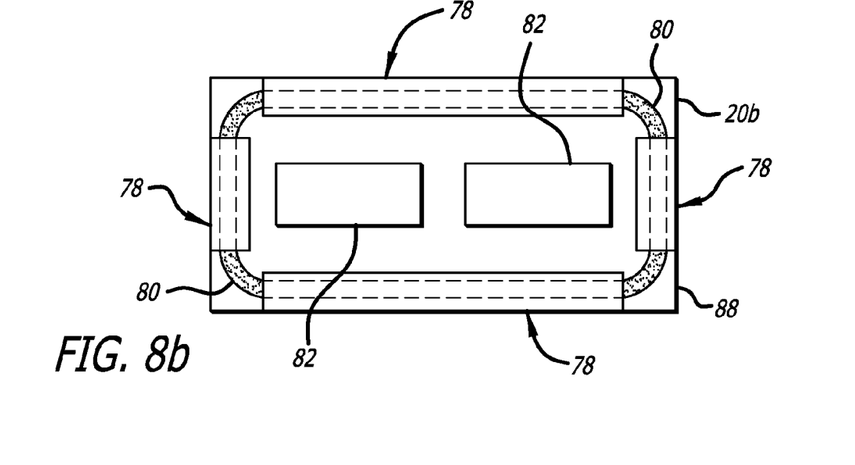
FIG. 8b is a plan view of a micropump according to one embodiment of the present invention.

Alternatively, as shown in FIG. 8a, the body 20a and the body 20b may be formed such that the bodies can be physically attached to one another. For example, body 20a comprises recesses 76 formed substantially around a perimeter of the body 20a. Body 20b, in turn, comprises binders 78 positioned also substantially around a perimeter of the body 20b. The binders 78 are deflectable and shaped to fit into the recesses 76 formed in the body 20a. When the disposable body 20a is to be mated with the non-disposable body 20b, the two bodies are pressed against one another thereby forcing the binders 78 to deflect outward around the base 84 of the body 20a until the binders 78 engage the recesses 76 of the body 20a. Once the binders 78 of the body 20b engage the recesses 76 of the body 20a, the two bodies are pulled towards one another and maintained in friction fit.

Electrical communication is established between bodies 20a and 20b through complementary electrodes 82 formed on the surface 86 of the body 20a and the surface 88 of the body 20b.

In certain embodiments of the present invention, is may be desirable to seal the electrodes 82 within a fluid tight environment. Accordingly, seal 80 may be embedded in the surface 86 of the body 20a and/or in the surface 88 of the body 20b. Upon mating of the two bodies 20a and 20b, the seal 80 is engaged and a fluid tight environment is established around the electrodes 82. The seal 80 may comprise a soft, yielding material such as Teflon, silicone, or other polymeric material. In order to prevent the seal 80 from moving, the seal may be embedded at least halfway into the surface in which it is attached.

It will be noted that because the piezoelectric body 32 vibrates during operation, the construction and mating of the bodies 20a and 20b must be sufficient to maintain the electrical communication between the bodies. For this, it is necessary that any wires with which the piezoelectric body 32 is connected to the electrodes of the body 20a be made from a material that is flexible, and which bonds strongly with the piezoelectric body.

In certain embodiments of the present invention, a user interface or indicator, not shown, is provided on the body 20b. The user interface may provide information such as the name and specifications of the fluid or pharmaceutical(s) being infused by the pump. The user interface may also be color-coded, so that the type of drug can be easily recognized. If multiple drugs are to be injected, in a system in which multiple infusion pumps 10 are employed, the user interface may provide pump identifiers that allow the user to easily identify a specific pump. The user interface may also provide warning lights that alert a user of particular operation parameters or operating conditions that have been encountered.

In yet another embodiment of the present invention, infusion pump 10 further comprises a control terminal, not shown, that is in electrical communication with the first and second circuits 70 and 72. The control terminal serves to provide control factors to the micropump 30. Micropump 30 control factors include, for example, the voltage V applied to the piezoelectric body 32 at the frequency n and the manner or rate at which the voltage V is increased and decreased during operation. The control terminal is in wireless or wired communication with the first and second circuits 70 and 72. In a one embodiment, a nurse or other caregiver may employ one control terminal to independently establish electrical communication with and thereby control a single infusion pump 10. Once the control factors have been provided to the infusion pump 10, the same control terminal may be carried or otherwise transported to a different infusion pump 10 in order to provide the control factors for the second infusion pump 10. Stated alternatively, it is contemplated that, for example, in a hospital setting, a plurality of different infusion pumps 10 can be controlled by a single control terminal. In such an embodiment, the control terminal may also serve to receive fluid flow rate data from the flow meter 74 associated with the infusion pump 10.

In another embodiment, the control terminal comprises a centralized patient fluid management system that is associated with a single patient during the course of the patient's treatment, i.e. the control terminal is not shared between multiple patients. In such an embodiment, the control terminal is operable to provide control factors to a plurality of infusion pumps 10, receive flow rate data from the flow meter 74, receive patient biological data from various patient sensors associated with the control terminal, and to provide various patient information to the caregiver based upon such patient data received. Such a control terminal is described in greater detail in the Assignee's U.S. patent application Ser. No. 12/972,374, entitled Patient Fluid Management System, filed Dec. 17, 2010.

Of particular significance, is the fact that the micropump 30 of the infusion pump 10 does not exchange data with the control terminal, i.e. the electrical communication between the micropump 30 and the control terminal is one-way, from the control terminal to the micropump 30. The micropump 30 is a slave to the control terminal. This configuration is advantageous because it provides for a simplified and more economical infusion pump 10. For example, by making the micropump 30 a slave of the control terminal, the circuitry within the micropump 30 is simplified and thereby more economical to manufacture. In view of the above described embodiments in which the micropump 30 is disposable, a hospital or clinic may more economically obtain the disposable portions of the infusion pump 10 and only have to acquire and maintain a limited number of the more complex and more costly control terminals.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An infusion pump comprising:
   a first fluid chamber channel;
   an inlet channel and an outlet channel, each formed on opposite sidewalls of the fluid chamber, the inlet channel and the outlet channel each continuously open to fluid flow and each comprising a differently configured channel constriction;
   the fluid chamber having a chamber depth that is shallowest proximate the inlet channel and deepest proximate the outlet channel; and
   a piezoelectric body having a first side attached to an exterior surface of the fluid chamber and a second side attached to an electrode.

2. The infusion pump of claim 1 wherein the first chamber depth varies at an angle greater than zero degrees and less than or equal to an angle of 10 degrees relative to an exterior surface of the chamber.

3. The infusion pump of claim 1 wherein the fluid chamber further comprises a length to width ratio of 4.

4. The infusion pump of claim 1 wherein a width of the inlet channel varies along at least two different lengths of the inlet channel.

5. The infusion pump of claim 1 wherein the fluid chamber is formed at least in part of a metal.

6. The infusion pump of claim 1 further comprising a second fluid chamber in fluid communication with the inlet channel and the outlet channel.

7. The infusion pump of claim 1 wherein a ratio of the dimension of the inlet channel constriction to a dimension of the inlet channel upstream of the inlet channel constriction is 0.13 to 0.67.

8. The infusion pump of claim 1 wherein an angle formed by opposite walls of the inlet channel between the inlet channel constriction and a fluid chamber inlet is approximately 0.0005 degrees.

9. The infusion pump of claim 1 further comprising a first body containing at least the piezoelectric body and a second body containing at least a power supply circuit.

10. The infusion pump of claim 9 wherein the first body is disposable.

11. A method for providing an infusion fluid to a patient:
maintaining open to continuous fluid flow an inlet channel and an outlet channel that are in fluid communication with a fluid chamber having a depth that is shallowest proximate the inlet channel and deepest proximate the outlet channel;
applying a voltage to a piezoelectric body attached to an exterior surface of the fluid chamber;
creating a resonance in a fluid in the fluid chamber;
constricting a dimension of the inlet channel and a dimension of the outlet channel differentially;
creating a net directional flow of the fluid out the outlet channel.

12. The method of claim 11 wherein the step of applying a voltage to a piezoelectric body attached to an exterior surface of the fluid chamber having a variable depth comprises applying a voltage in the range of 20 to 100 volts.

13. The method of claim 11 wherein the step of applying a voltage to a piezoelectric body attached to an exterior surface of the fluid chamber having a variable depth comprises controlling the rate of rise of voltage, wherein the rate of rise forms an angle relative to a vertical line in the range of 3 to 45 degrees.

14. The method of claim 11 wherein the step of applying a voltage to a piezoelectric body attached to an exterior surface of the fluid chamber comprises applying a voltage at a frequency in the range of 50 to 4500 Hz.

15. The method of claim 11 wherein the step of creating a resonance in a fluid in the fluid chamber comprises controlling selectively at least two of the variable selected from the group consisting of: (1) a ratio of the dimension of an inlet channel constriction to a dimension of an inlet channel upstream of the inlet channel constriction; (2) a length to width ratio of the fluid chamber; and (3) a variation in a fluid chamber depth along a length of the fluid chamber, in order maximize a fluid flow while minimizing vaporization of dissolved gas.

* * * * *

UNITED STATES PATENT AND TRADEMARK OFFICE
CERTIFICATE OF CORRECTION

PATENT NO. : 8,353,872 B2
APPLICATION NO. : 13/292710
DATED : January 15, 2013
INVENTOR(S) : Yasuhiro Kawamura It is certified that error appears in the above-identified patent and that said Letters Patent is hereby corrected as shown below:

Column 10, line 45, cancel the word "channel".

Column 12, line 5 and line 9, cancel the text "having a variable depth".

Signed and Sealed this
Second Day of April, 2013

Teresa Stanek Rea
*Acting Director of the United States Patent and Trademark Office*